(12) United States Patent
Pett et al.

(10) Patent No.: US 11,759,235 B2
(45) Date of Patent: Sep. 19, 2023

(54) CONSTANT-TORQUE INTRAOSSEOUS ACCESS DEVICES AND METHODS THEREOF

(71) Applicant: Bard Access Systems, Inc., Salt Lake City, UT (US)

(72) Inventors: Daniel Pett, Sandy, UT (US); Daniel B. Blanchard, Bountiful, UT (US); Eric W. Lindekugel, Salt Lake City, UT (US); Joe Spataro, Cottonwood Heights, UT (US); Ralph Sonderegger, Farmington, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 339 days.

(21) Appl. No.: 17/035,272

(22) Filed: Sep. 28, 2020

(65) Prior Publication Data
US 2021/0093356 A1    Apr. 1, 2021

Related U.S. Application Data

(60) Provisional application No. 62/907,454, filed on Sep. 27, 2019.

(51) Int. Cl.
*A61B 17/34* (2006.01)
*A61B 17/16* (2006.01)

(52) U.S. Cl.
CPC ........ *A61B 17/3472* (2013.01); *A61B 17/164* (2013.01); *A61B 17/1624* (2013.01)

(58) Field of Classification Search
CPC ............ A61B 17/3472; A61B 17/3478; A61B 17/3423; A61B 2017/348;

(Continued)

(56) References Cited

U.S. PATENT DOCUMENTS 2,773,501 A    12/1956 Young
3,071,135 A    1/1963 Baldwin et al.
(Continued)

FOREIGN PATENT DOCUMENTS

CN    108742795 A    11/2018
CN    110547847 A    12/2019
(Continued)

OTHER PUBLICATIONS

U.S. Appl. No. 17/031,650, filed Sep. 24, 2020 Notice of Allowance dated Oct. 12, 2022.

(Continued)

*Primary Examiner* — Matthew J Lawson
(74) *Attorney, Agent, or Firm* — Rutan & Tucker LLP

(57) ABSTRACT

Constant-torque intraosseous access devices and methods thereof are disclosed. An intraosseous access device can include a constant-torque spring assembly disposed in a housing, a drive shaft extending from the housing, and an intraosseous needle coupled to the drive shaft configured to provide intraosseous access to a medullary cavity of a patient. A method of such an intraosseous access device can include inserting a distal end of the intraosseous needle through skin at an insertion site of a patient; applying force to bone at the insertion site with the distal end of the intraosseous needle, which starts winding a metal ribbon of the constant-torque spring assembly from an output spool onto a storage spool, thereby starting rotation of the intraosseous needle; and drilling through the bone until the intraosseous needle enters a medullary cavity of the patient, thereby achieving intraosseous access with the intraosseous access device.

19 Claims, 6 Drawing Sheets

(58) Field of Classification Search
CPC ........ A61B 2017/3494; A61B 17/1604; A61B 17/1637; A61B 17/1635; A61B 17/164
See application file for complete search history.

(56) References Cited

U.S. PATENT DOCUMENTS

| | | | |
|---|---|---|---|
| 3,804,544 A | 4/1974 | Adams | |
| 3,811,442 A | 5/1974 | Maroth | |
| 3,815,605 A | 6/1974 | Schmidt et al. | |
| 3,991,765 A | 11/1976 | Cohen | |
| 4,266,555 A | 5/1981 | Jamshidi | |
| 4,314,565 A | 2/1982 | Lee | |
| 4,383,530 A | 5/1983 | Bruno | |
| 4,736,742 A | 4/1988 | Alexson et al. | |
| 4,889,529 A | 12/1989 | Haindl | |
| 4,952,207 A | 8/1990 | Lemieux | |
| 4,964,854 A | 10/1990 | Luther | |
| 4,969,870 A | 11/1990 | Kramer et al. | |
| 5,040,542 A | 8/1991 | Gray | |
| 5,042,558 A | 8/1991 | Hussey et al. | |
| 5,053,017 A | 10/1991 | Chamuel | |
| 5,122,114 A | 6/1992 | Miller et al. | |
| 5,207,697 A | 5/1993 | Carusillo et al. | |
| 5,263,939 A | 11/1993 | Wortrich | |
| 5,290,267 A | 3/1994 | Zimmermann | |
| 5,312,364 A | 5/1994 | Jacobs | |
| 5,332,398 A | 7/1994 | Miller et al. | |
| 5,364,367 A | 11/1994 | Banks et al. | |
| 5,372,583 A | 12/1994 | Roberts et al. | |
| 5,406,940 A | 4/1995 | Melzer et al. | |
| 5,451,210 A | 9/1995 | Kramer et al. | |
| 5,554,154 A | 9/1996 | Rosenberg | |
| 5,575,780 A | 11/1996 | Saito | |
| 5,591,188 A | 1/1997 | Waisman | |
| 5,601,559 A | 2/1997 | Melker et al. | |
| 5,667,509 A | 9/1997 | Westin | |
| 5,688,249 A | 11/1997 | Chang et al. | |
| 5,779,708 A | 7/1998 | Wu | |
| 5,817,052 A | 10/1998 | Johnson et al. | |
| 5,853,393 A | 12/1998 | Bogert | |
| 5,868,711 A | 2/1999 | Kramer et al. | |
| 5,885,293 A | 3/1999 | McDevitt | |
| 5,927,976 A | 7/1999 | Wu | |
| 5,960,797 A | 10/1999 | Kramer et al. | |
| 5,967,143 A | 10/1999 | Klappenberger | |
| 6,117,108 A | 9/2000 | Woehr et al. | |
| 6,135,769 A | 10/2000 | Kwan | |
| 6,199,664 B1 * | 3/2001 | Tkaczyk | F03G 1/00 185/39 |
| 6,210,373 B1 | 4/2001 | Allmon | |
| 6,228,088 B1 | 5/2001 | Miller et al. | |
| 6,247,928 B1 | 6/2001 | Meller et al. | |
| 6,270,484 B1 | 8/2001 | Yoon | |
| 6,273,715 B1 | 8/2001 | Meller et al. | |
| 6,419,490 B1 | 7/2002 | Kitchings Weathers, Jr. | |
| 6,458,117 B1 | 10/2002 | Pollins, Sr. | |
| 6,527,778 B2 | 3/2003 | Athanasiou et al. | |
| 6,602,214 B2 | 8/2003 | Heinz et al. | |
| 6,626,887 B1 | 9/2003 | Wu | |
| 6,629,959 B2 | 10/2003 | Kuracina et al. | |
| 6,641,395 B2 | 11/2003 | Kumar et al. | |
| 6,652,490 B2 | 11/2003 | Howell | |
| 6,692,471 B2 | 2/2004 | Boudreaux | |
| 6,761,726 B1 | 7/2004 | Findlay et al. | |
| 6,814,734 B2 | 11/2004 | Chappuis et al. | |
| 6,830,562 B2 | 12/2004 | Mogensen et al. | |
| 6,875,219 B2 | 4/2005 | Arramon et al. | |
| 6,905,486 B2 | 6/2005 | Gibbs | |
| 6,916,292 B2 | 7/2005 | Morawski et al. | |
| 6,984,213 B2 | 1/2006 | Horner et al. | |
| 6,997,907 B2 | 2/2006 | Safabash et al. | |
| 7,112,191 B2 | 9/2006 | Daga | |
| 7,135,031 B2 | 11/2006 | Flint | |
| 7,214,208 B2 | 5/2007 | Vaillancourt et al. | |
| 7,347,838 B2 | 3/2008 | Kulli | |
| 7,347,840 B2 | 3/2008 | Findlay et al. | |
| 7,407,493 B2 | 8/2008 | Cane' | |
| 7,458,954 B2 | 12/2008 | Ferguson et al. | |
| 7,513,888 B2 | 4/2009 | Sircom et al. | |
| 7,530,965 B2 | 5/2009 | Villa et al. | |
| 7,534,227 B2 | 5/2009 | Kulli | |
| 7,569,033 B2 | 8/2009 | Greene et al. | |
| 7,582,102 B2 | 9/2009 | Heinz et al. | |
| 7,588,559 B2 | 9/2009 | Aravena et al. | |
| 7,658,725 B2 | 2/2010 | Bialecki et al. | |
| 7,670,328 B2 | 3/2010 | Miller | |
| 7,699,807 B2 | 4/2010 | Faust et al. | |
| 7,699,850 B2 | 4/2010 | Miller | |
| 7,736,332 B2 | 6/2010 | Carlyon et al. | |
| 7,749,225 B2 | 7/2010 | Chappuis et al. | |
| 7,798,994 B2 | 9/2010 | Brimhall | |
| 7,811,260 B2 | 10/2010 | Miller et al. | |
| 7,815,642 B2 | 10/2010 | Miller | |
| 7,828,774 B2 | 11/2010 | Harding et al. | |
| 7,833,204 B2 | 11/2010 | Picha | |
| 7,842,038 B2 | 11/2010 | Haddock et al. | |
| 7,850,620 B2 | 12/2010 | Miller et al. | |
| 7,850,650 B2 | 12/2010 | Breitweiser | |
| D633,199 S | 2/2011 | MacKay et al. | |
| 7,899,528 B2 | 3/2011 | Miller et al. | |
| 7,905,857 B2 | 3/2011 | Swisher | |
| 7,951,089 B2 | 5/2011 | Miller | |
| 7,955,297 B2 | 6/2011 | Radmer et al. | |
| 7,972,339 B2 | 7/2011 | Nassiri et al. | |
| 7,976,502 B2 | 7/2011 | Baid | |
| 8,038,664 B2 | 10/2011 | Miller et al. | |
| 8,043,253 B2 | 10/2011 | Kraft et al. | |
| 8,043,265 B2 | 10/2011 | Abe et al. | |
| 8,142,365 B2 | 3/2012 | Miller | |
| 8,152,771 B2 | 4/2012 | Mogensen et al. | |
| 8,162,904 B2 | 4/2012 | Takano et al. | |
| 8,167,899 B2 | 5/2012 | Justis et al. | |
| 8,235,945 B2 | 8/2012 | Baid | |
| 8,246,584 B2 | 8/2012 | Aravena et al. | |
| 8,273,053 B2 | 9/2012 | Saltzstein | |
| 8,292,891 B2 | 10/2012 | Browne et al. | |
| 8,308,693 B2 | 11/2012 | Miller et al. | |
| 8,333,769 B2 | 12/2012 | Browne et al. | |
| 8,356,598 B2 | 1/2013 | Rumsey | |
| 8,357,163 B2 | 1/2013 | Sidebotham et al. | |
| 8,388,541 B2 | 3/2013 | Messerly et al. | |
| 8,388,623 B2 | 3/2013 | Browne et al. | |
| 8,414,539 B1 | 4/2013 | Kuracina et al. | |
| 8,419,683 B2 | 4/2013 | Miller et al. | |
| 8,480,632 B2 | 7/2013 | Miller et al. | |
| 8,480,672 B2 | 7/2013 | Browne et al. | |
| 8,486,027 B2 | 7/2013 | Findlay et al. | |
| 8,506,568 B2 | 8/2013 | Miller | |
| 8,535,271 B2 | 9/2013 | Fuchs et al. | |
| 8,562,615 B2 | 10/2013 | Browne et al. | |
| 8,641,715 B2 | 2/2014 | Miller | |
| 8,647,257 B2 | 2/2014 | Jansen et al. | |
| 8,656,929 B2 | 2/2014 | Miller et al. | |
| 8,657,790 B2 | 2/2014 | Tal et al. | |
| 8,663,231 B2 | 3/2014 | Browne et al. | |
| 8,668,698 B2 | 3/2014 | Miller et al. | |
| 8,684,978 B2 | 4/2014 | Miller et al. | |
| 8,690,791 B2 | 4/2014 | Miller | |
| 8,715,287 B2 | 5/2014 | Miller | |
| 8,771,230 B2 | 7/2014 | White et al. | |
| 8,781,555 B2 | 7/2014 | Burnside et al. | |
| 8,801,663 B2 | 8/2014 | Woehr | |
| 8,812,101 B2 | 8/2014 | Miller et al. | |
| 8,814,835 B2 | 8/2014 | Baid | |
| 8,821,493 B2 | 9/2014 | Anderson | |
| 8,828,001 B2 | 9/2014 | Stearns et al. | |
| 8,849,382 B2 | 9/2014 | Cox et al. | |
| 8,870,872 B2 | 10/2014 | Miller | |
| 8,936,575 B2 | 1/2015 | Moulton | |
| 8,944,069 B2 | 2/2015 | Miller et al. | |
| 8,974,410 B2 | 3/2015 | Miller et al. | |
| 8,998,848 B2 | 4/2015 | Miller et al. | |
| 9,072,543 B2 | 7/2015 | Miller et al. | |
| 9,078,637 B2 | 7/2015 | Miller | |

(56) References Cited

U.S. PATENT DOCUMENTS

| | | |
|---|---|---|
| 9,149,625 B2 | 10/2015 | Woehr et al. |
| 9,173,679 B2 | 11/2015 | Tzachar et al. |
| 9,226,756 B2 | 1/2016 | Teisen et al. |
| 9,278,195 B2 | 3/2016 | Erskine |
| 9,295,487 B2 | 3/2016 | Miller et al. |
| 9,302,077 B2 | 4/2016 | Domonkos et al. |
| 9,314,232 B2 | 4/2016 | Stark |
| 9,314,270 B2 | 4/2016 | Miller |
| 9,358,348 B2 | 6/2016 | Weilbacher et al. |
| 9,393,031 B2 | 7/2016 | Miller |
| 9,414,815 B2 | 8/2016 | Miller et al. |
| 9,415,192 B2 | 8/2016 | Kuracina et al. |
| 9,421,345 B2 | 8/2016 | Woehr et al. |
| 9,427,555 B2 | 8/2016 | Baid |
| 9,433,400 B2 | 9/2016 | Miller |
| 9,439,667 B2 | 9/2016 | Miller |
| 9,439,702 B2 | 9/2016 | Arthur et al. |
| 9,445,743 B2 | 9/2016 | Kassab |
| 9,451,968 B2 | 9/2016 | Miller et al. |
| 9,451,983 B2 | 9/2016 | Windolf |
| 9,456,766 B2 | 10/2016 | Cox et al. |
| 9,480,483 B2 | 11/2016 | Browne et al. |
| 9,492,097 B2 | 11/2016 | Wilkes et al. |
| 9,504,477 B2 | 11/2016 | Miller et al. |
| 9,521,961 B2 | 12/2016 | Silverstein et al. |
| 9,545,243 B2 | 1/2017 | Miller et al. |
| 9,554,716 B2 | 1/2017 | Burnside et al. |
| 9,615,816 B2 | 4/2017 | Woodard |
| 9,615,838 B2 | 4/2017 | Nino et al. |
| 9,623,210 B2 | 4/2017 | Woehr |
| 9,636,031 B2 | 5/2017 | Cox |
| 9,636,484 B2 | 5/2017 | Baid |
| 9,649,048 B2 | 5/2017 | Cox et al. |
| 9,681,889 B1 | 6/2017 | Greenhalgh et al. |
| 9,687,633 B2 | 6/2017 | Teoh |
| 9,717,564 B2 | 8/2017 | Miller et al. |
| 9,730,729 B2 | 8/2017 | Kilcoin et al. |
| 9,782,546 B2 | 10/2017 | Woehr |
| 9,839,740 B2 | 12/2017 | Beamer et al. |
| 9,844,646 B2 | 12/2017 | Knutsson |
| 9,844,647 B2 | 12/2017 | Knutsson |
| 9,872,703 B2 | 1/2018 | Miller et al. |
| 9,883,853 B2 | 2/2018 | Woodard et al. |
| 9,895,512 B2 | 2/2018 | Kraft et al. |
| 9,962,211 B2 | 5/2018 | Csematoni |
| 10,052,111 B2 | 8/2018 | Miller et al. |
| 10,092,320 B2 | 10/2018 | Morgan et al. |
| 10,159,531 B2 | 12/2018 | Misener et al. |
| 10,172,538 B2 | 1/2019 | Kassab |
| 10,413,211 B2 | 9/2019 | Kassab |
| 10,449,330 B2 | 10/2019 | Newman et al. |
| 10,893,887 B2 | 1/2021 | Blanchard |
| 10,980,522 B2 | 4/2021 | Muse |
| 2003/0060781 A1 | 3/2003 | Mogensen et al. |
| 2003/0225344 A1 | 12/2003 | Miller |
| 2003/0225411 A1 | 12/2003 | Miller |
| 2003/0229308 A1 | 12/2003 | Tsals et al. |
| 2004/0010236 A1 | 1/2004 | Morawski et al. |
| 2004/0059317 A1 | 3/2004 | Hermann |
| 2004/0220497 A1 | 11/2004 | Findlay et al. |
| 2004/0243135 A1 | 12/2004 | Koseki |
| 2005/0035014 A1 | 2/2005 | Cane |
| 2005/0101912 A1 | 5/2005 | Faust et al. |
| 2005/0113866 A1 | 5/2005 | Heinz et al. |
| 2005/0131345 A1 | 6/2005 | Miller |
| 2005/0165403 A1* | 7/2005 | Miller ............. A61B 10/025 600/567 |
| 2006/0015066 A1 | 1/2006 | Turieo et al. |
| 2006/0025723 A1 | 2/2006 | Ballarini |
| 2006/0058826 A1* | 3/2006 | Evans ............. A61B 17/3472 606/170 |
| 2007/0049945 A1 | 3/2007 | Miller |
| 2007/0191772 A1 | 8/2007 | Wojcik |
| 2007/0270775 A1 | 11/2007 | Miller et al. |
| 2008/0015467 A1 | 1/2008 | Miller |
| 2008/0154304 A1 | 6/2008 | Crawford et al. |
| 2008/0208136 A1 | 8/2008 | Findlay et al. |
| 2008/0215056 A1 | 9/2008 | Miller et al. |
| 2008/0221580 A1 | 9/2008 | Miller et al. |
| 2008/0257359 A1 | 10/2008 | Rumsey |
| 2009/0048575 A1 | 2/2009 | Waters |
| 2009/0054808 A1 | 2/2009 | Miller |
| 2009/0093830 A1 | 4/2009 | Miller |
| 2009/0204024 A1 | 8/2009 | Miller |
| 2009/0306697 A1 | 12/2009 | Fischvogt |
| 2010/0004606 A1 | 1/2010 | Hansen et al. |
| 2010/0204649 A1 | 8/2010 | Miller et al. |
| 2010/0286607 A1 | 11/2010 | Saltzstein |
| 2010/0298830 A1 | 11/2010 | Browne et al. |
| 2010/0298831 A1 | 11/2010 | Browne et al. |
| 2010/0312246 A1 | 12/2010 | Browne et al. |
| 2011/0004163 A1 | 1/2011 | Vaidya |
| 2011/0028976 A1 | 2/2011 | Miller |
| 2012/0202180 A1 | 8/2012 | Stock et al. |
| 2012/0203154 A1 | 8/2012 | Tzachar |
| 2012/0274280 A1 | 11/2012 | Yip et al. |
| 2013/0030439 A1 | 1/2013 | Browne et al. |
| 2013/0041345 A1 | 2/2013 | Kilcoin et al. |
| 2013/0072938 A1 | 3/2013 | Browne et al. |
| 2013/0102924 A1 | 4/2013 | Findlay et al. |
| 2013/0158484 A1 | 6/2013 | Browne et al. |
| 2013/0178807 A1 | 7/2013 | Baid |
| 2014/0031674 A1 | 1/2014 | Newman et al. |
| 2014/0031794 A1 | 1/2014 | Windolf |
| 2014/0039400 A1 | 2/2014 | Browne et al. |
| 2014/0081281 A1 | 3/2014 | Felder |
| 2014/0142577 A1 | 5/2014 | Miller |
| 2014/0171873 A1 | 6/2014 | Mark |
| 2014/0188133 A1 | 7/2014 | Misener |
| 2014/0262408 A1 | 9/2014 | Woodard |
| 2014/0262880 A1 | 9/2014 | Yoon |
| 2014/0276205 A1 | 9/2014 | Miller et al. |
| 2014/0276206 A1 | 9/2014 | Woodward et al. |
| 2014/0276471 A1 | 9/2014 | Emery et al. |
| 2014/0276833 A1 | 9/2014 | Larsen et al. |
| 2014/0276839 A1 | 9/2014 | Forman et al. |
| 2014/0343454 A1 | 11/2014 | Miller et al. |
| 2014/0343497 A1 | 11/2014 | Baid |
| 2015/0011941 A1 | 1/2015 | Saeki |
| 2015/0045732 A1 | 2/2015 | Murphy et al. |
| 2015/0080762 A1 | 3/2015 | Kassab et al. |
| 2015/0126931 A1 | 5/2015 | Holm et al. |
| 2015/0196737 A1 | 7/2015 | Baid |
| 2015/0223786 A1 | 8/2015 | Morgan et al. |
| 2015/0230823 A1 | 8/2015 | Morgan et al. |
| 2015/0238733 A1 | 8/2015 | bin Abdulla |
| 2015/0342615 A1 | 12/2015 | Keinan et al. |
| 2015/0342756 A1 | 12/2015 | Bays et al. |
| 2015/0351797 A1 | 12/2015 | Miller et al. |
| 2015/0366569 A1 | 12/2015 | Miller |
| 2016/0022282 A1 | 1/2016 | Miller et al. |
| 2016/0022284 A1 | 1/2016 | Lele et al. |
| 2016/0058432 A1 | 3/2016 | Miller |
| 2016/0066954 A1 | 3/2016 | Miller et al. |
| 2016/0136410 A1 | 5/2016 | Aklog et al. |
| 2016/0183974 A1 | 6/2016 | Miller |
| 2016/0184509 A1 | 6/2016 | Miller et al. |
| 2016/0235949 A1 | 8/2016 | Baid |
| 2016/0305497 A1* | 10/2016 | Victor ............. F16D 7/024 |
| 2016/0354539 A1 | 12/2016 | Tan et al. |
| 2016/0361519 A1 | 12/2016 | Teoh et al. |
| 2017/0020533 A1 | 1/2017 | Browne et al. |
| 2017/0020560 A1 | 1/2017 | Van Citters et al. |
| 2017/0021138 A1 | 1/2017 | Sokolski |
| 2017/0043135 A1 | 2/2017 | Knutsson |
| 2017/0105763 A1 | 4/2017 | Karve et al. |
| 2017/0136217 A1 | 5/2017 | Riesenberger et al. |
| 2017/0151419 A1 | 6/2017 | Sonksen |
| 2017/0156740 A9 | 6/2017 | Stark |
| 2017/0156751 A1 | 6/2017 | Csematoni |
| 2017/0209129 A1 | 7/2017 | Fagundes et al. |
| 2017/0231644 A1 | 8/2017 | Anderson |
| 2017/0303962 A1 | 10/2017 | Browne et al. |
| 2017/0303963 A1 | 10/2017 | Kilcoin et al. |

(56) References Cited

U.S. PATENT DOCUMENTS

| | | |
|---|---|---|
| 2018/0049772 A1 | 2/2018 | Brockman et al. |
| 2018/0092662 A1 | 4/2018 | Rioux et al. |
| 2018/0116551 A1 | 5/2018 | Newman et al. |
| 2018/0116642 A1 | 5/2018 | Woodard et al. |
| 2018/0116693 A1 | 5/2018 | Blanchard et al. |
| 2018/0117262 A1 | 5/2018 | Islam |
| 2018/0125465 A1 | 5/2018 | Muse et al. |
| 2018/0153474 A1 | 6/2018 | Aeschlimann et al. |
| 2018/0154112 A1 | 6/2018 | Chan et al. |
| 2018/0221003 A1 | 8/2018 | Hibner et al. |
| 2018/0228509 A1* | 8/2018 | Fojtik ............... A61B 17/3472 |
| 2018/0242982 A1 | 8/2018 | Laughlin et al. |
| 2019/0069812 A1 | 3/2019 | Isaacson et al. |
| 2019/0175220 A1 | 6/2019 | Coppedge et al. |
| 2019/0282244 A1* | 9/2019 | Muse ..................... A61C 3/02 |
| 2020/0054347 A1 | 2/2020 | Coppedge et al. |
| 2020/0054410 A1 | 2/2020 | Pfotenhauer et al. |
| 2020/0113584 A1 | 4/2020 | McGinley et al. |
| 2020/0129186 A1 | 4/2020 | Miller et al. |
| 2020/0197121 A1 | 6/2020 | Morey et al. |
| 2021/0093357 A1 | 4/2021 | Pett et al. |
| 2021/0093358 A1 | 4/2021 | Lindekugel et al. |
| 2021/0282812 A1* | 9/2021 | Tierney ............. A61B 17/1624 |
| 2021/0322055 A1 | 10/2021 | Lindekugel et al. |
| 2021/0375445 A1 | 12/2021 | Lindekugel et al. |
| 2022/0240976 A1 | 8/2022 | Pett et al. |
| 2022/0249104 A1 | 8/2022 | Pett et al. |
| 2023/0106545 A1 | 4/2023 | Pett et al. |

FOREIGN PATENT DOCUMENTS

| | | |
|---|---|---|
| EP | 0923961 A1 | 6/1999 |
| ES | 2390297 A1 | 11/2012 |
| FR | 2581548 A1 | 11/1986 |
| JP | 2018509969 A | 4/2018 |
| WO | 1997024151 A1 | 7/1997 |
| WO | 1998052638 A3 | 2/1999 |
| WO | 2005/046769 A2 | 5/2005 |
| WO | 05041790 A2 | 5/2005 |
| WO | 2005053506 A2 | 6/2005 |
| WO | 2005072625 A2 | 8/2005 |
| WO | 2007018809 A2 | 2/2007 |
| WO | 2008002961 A2 | 1/2008 |
| WO | 2008016757 A2 | 2/2008 |
| WO | 08033873 A2 | 3/2008 |
| WO | 2008033871 A2 | 3/2008 |
| WO | 2008033872 A2 | 3/2008 |
| WO | 2008033874 A2 | 3/2008 |
| WO | 2008054894 A2 | 5/2008 |
| WO | 2008086258 A1 | 7/2008 |
| WO | 2008124206 A2 | 10/2008 |
| WO | 2008124463 A2 | 10/2008 |
| WO | 2008130893 A1 | 10/2008 |
| WO | 2008134355 A2 | 11/2008 |
| WO | 2008144379 A2 | 11/2008 |
| WO | 2009070896 A1 | 6/2009 |
| WO | 2010043043 A2 | 4/2010 |
| WO | 2011097311 A2 | 8/2011 |
| WO | 2011139294 A1 | 11/2011 |
| WO | 2013009901 A2 | 1/2013 |
| WO | 2013173360 A1 | 11/2013 |
| WO | 2014142948 A1 | 9/2014 |
| WO | 2014144239 A1 | 9/2014 |
| WO | 2014144262 A1 | 9/2014 |
| WO | 2014144489 A2 | 9/2014 |
| WO | 2014144757 A1 | 9/2014 |
| WO | 2014144797 A1 | 9/2014 |
| WO | 2015/177612 A1 | 11/2015 |
| WO | 16033016 A1 | 3/2016 |
| WO | 16053834 A1 | 4/2016 |
| WO | 2016/085973 A1 | 6/2016 |
| WO | 2016163939 A1 | 10/2016 |
| WO | 18006045 A1 | 1/2018 |
| WO | 2018025094 A1 | 2/2018 |
| WO | 2018058036 A1 | 3/2018 |
| WO | 2018075694 A1 | 4/2018 |
| WO | 18098086 A1 | 5/2018 |
| WO | 2018165334 A1 | 9/2018 |
| WO | 2018165339 A1 | 9/2018 |
| WO | 2019051343 A1 | 3/2019 |
| WO | 2019/164990 A1 | 8/2019 |
| WO | 2021/011795 A1 | 1/2021 |
| WO | 2021/016122 A1 | 1/2021 |
| WO | 2021/062385 A1 | 4/2021 |
| WO | 2021062038 A1 | 4/2021 |
| WO | 2021062394 A1 | 4/2021 |
| WO | 2022/165232 A1 | 8/2022 |
| WO | 2022/170269 A1 | 8/2022 |

OTHER PUBLICATIONS

U.S. Appl. No. 17/035,336, filed Sep. 28, 2020 Notice of Allowance dated Jan. 11, 2023.
PCT/US2022/014391 filed Jan. 28, 2022 International Search Report and Written Opinion dated Apr. 14, 2022.
PCT/US2022/015686 filed Feb. 8, 2022 International Search Report and Written Opinion dated May 25, 2022.
U.S. Appl. No. 17/031,650, filed Sep. 24, 2020 Final Office Action dated Jul. 20, 2022.
U.S. Appl. No. 17/035,336, filed Sep. 28, 2020 Restriction Requirement dated Jul. 26, 2022.
PCT/US2021/028114 filed Apr. 20, 2021 International Search Report and Written Opinion dated Jul. 12, 2021.
PCT/US2021/ 046573 filed Aug. 18, 2021 International Search Report and Written Opinion dated Nov. 30, 2021.
PCT/US2021/ 047378 filed Aug. 24, 2021 International Search Report and Written Opinion dated Nov. 17, 2021.
PCT/US2021/ 048542 filed Aug. 31, 2021 International Search Report and Written Opinion dated Dec. 9, 2021.
PCT/US2021/ 049475 filed Sep. 8, 2021 International Search Report and Written Opinion dated Dec. 9, 2021.
U.S. Appl. No. 17/031,650 filed Sep. 24, 2020 Non-Final Office Action dated Jan. 19, 2022.
PCT/US2019/ 018828 filed Feb. 20, 2019 International Preliminary Report on Patentability dated Aug. 27, 2020.
PCT/US2019/ 018828 filed Feb. 20, 2019 International Search Report and Written Opinion dated Jun. 13, 2019.
Ekchian Gregory James et al: "Quantitative Methods for In Vitro and In Vivo Characterization of Cell and Tissue Metabolism", Jun. 11, 2018, XP055839281, retrieved from the internet on Sep. 8, 2021 : URL: https://dspace.mit.edu/bitstream/handle/1721.1/117890/1051211749-MIT.pdf?sequence=1&isAllowed=y.
PCT/US2021/ 035232 filed Jun. 1, 2021 International Search Report and Written Opinion dated Oct. 19, 2021.
PCT/US2021/035475 filed Jun. 2, 2021 International Search Report and Written Opinion dated Sep. 17, 2021.
PCT/US2020/ 053119 filed Sep. 28, 2020 International Search Report and Written Opinion dated Jan. 5, 2021.
PCT/US2020/052558 filed Sep. 24, 2020 International Search Report and Written Opinion dated Feb. 11, 2021.
PCT/US2020/053135 filed Sep. 28, 2020 International Search Report and Written Opinion dated Dec. 18, 2020.
U.S. Appl. No. 17/235,134, filed Apr. 20, 2021 Restriction Requirement dated Mar. 7, 2023.
U.S. Appl. No. 17/337,100, filed Jun. 2, 2021 Non-Final Office Action dated Jun. 2, 2023.
U.S. Appl. No. 17/667,291, filed Feb. 8, 2022 Restriction Requirement dated May 31, 2023.

* cited by examiner

CONSTANT-TORQUE INTRAOSSEOUS ACCESS DEVICES AND METHODS THEREOF

PRIORITY

This application claims the benefit of priority to U.S. Provisional Application No. 62/907,454, filed Sep. 27, 2019, which is incorporated by reference in its entirety into this application.

BACKGROUND

Peripheral intravenous catheter ("PIVC") insertions are increasingly challenging in emergency scenarios as critically ill patients deteriorate. Intraosseous ("IO") access is often the only means available to clinicians to increase the patient's chances of recovery and even save the patients' lives.

IO access can be acquired in as little as 2-5 seconds with a relatively high chance of success. The commercial state-of-the-art medical device for 10 access is a small, drill-like device built around a relatively primitive electric motor. Motors such as the foregoing provide an adequate means for drilling to effectuate IO access, but such motors are not necessarily tuned to the needs of IO access. The infrastructure of such motors (e.g., batteries, wires, gear trains, gear-reduction hardware, switches, etc.) is largely overbuilt for just 1-2 seconds of drilling. Additionally, the drill-like device and the motors thereof must be monitored and managed by clinical personnel for readiness, and there are requirements and regulations related to the disposal of the foregoing medical devices. What is needed is needed is a better tuned medical device that significantly reduces design and manufacturing complexity while optimizing user experience.

Disclosed herein are constant-torque IO access devices and methods thereof that address the forgoing shortcomings.

SUMMARY

Disclosed herein is an IO access device including, in some embodiments, a constant-torque spring assembly disposed in a housing, a drive shaft extending from the housing, and an IO needle coupled to the drive shaft. The drive shaft is coupled to the constant-torque spring. The IO needle is configured to provide IO access to a medullary cavity of a patient.

In some embodiments, the constant-torque spring assembly includes a metal ribbon reversely wound onto an output spool. The metal ribbon is configured to wind onto a storage spool with a constant torque when the output spool is released.

In some embodiments, spindles of the output spool and the storage spool are coupled together by at least one elastomeric loop to prevent any timing-related errors between the output spool and the storage spool.

In some embodiments, the housing includes a set of housing teeth around an aperture of the housing from which the drive shaft extends. The drive shaft includes a set of complementary drive-shaft teeth around the drive shaft opposing the set of housing teeth. The set of housing teeth and the set of drive-shaft teeth engage in an inactive state of the IO access device by a compression spring between a back side of the set of drive-shaft teeth and the output spool.

In some embodiments, the drive shaft is slideably disposed in an axial channel of the output spool such that force applied to a distal end of the IO needle simultaneously compresses the compression spring and inserts the drive shaft deeper into the axial channel. This disengages the set of drive-shaft teeth from the set of housing teeth and initiates an active state of the IO access device. In the active state of the IO access device, rotation of the IO needle is effectuated by the output spool of the constant-torque spring assembly on the drive shaft.

In some embodiments, a combination of a molded piece within the housing and an extension pin disposed in the axial channel of the output spool between the drive shaft and the molded piece is configured to stop over insertion of the drive shaft into the axial channel of the output spool. In addition, the combination of the extension pin and the molded piece is configured to decouple the force applied to the distal end of the IO needle from the constant-torque spring assembly.

In some embodiments, the compression spring is configured to relax when the force applied to the distal end of the IO needle is removed. This reengages the set of drive-shaft teeth with the set of housing teeth and reinitiates the inactive state of the IO access device.

In some embodiments, the IO access device is configured such that entry of the IO needle into the medullary cavity of the patient automatically removes the force applied to the distal end of the IO needle.

In some embodiments, the IO access device further includes an interlock including a trigger and a lock pin disposed between the trigger and the output spool in the inactive state of the IO access device. The trigger is configured to release the lock pin allowing the force applied to the distal end of the IO needle to simultaneously compress the compression spring and insert the drive shaft deeper into the axial channel.

In some embodiments, the IO access device further includes a braking system configured to act on the output spool to slow the metal ribbon from winding onto the storage spool.

In some embodiments, the IO needle is configured to separate from the IO access device subsequent to achieving IO access to the medullary cavity of the patient.

In some embodiments, the IO needle includes an obturator removably disposed in a cannula. The cannular has a lumen configured for at least interosseous infusion upon removal of the obturator.

Also disclosed herein is an IO access device including, in some embodiments, a constant-torque spring assembly disposed in a housing, a drive shaft extending from the housing, and an IO needle coupled to the drive shaft configured to provide IO access to a medullary cavity of a patient. The constant-torque spring assembly includes a metal ribbon reversely wound onto an output spool. The metal ribbon is configured to wind onto a storage spool from the output spool with a constant torque in an active state of the IO access device. The drive shaft is slideably disposed in an axial channel of the output spool. Force applied to a distal-end portion of the drive shaft simultaneously compresses a compression spring and inserts the drive shaft deeper into the axial channel. This disengages a set of drive-shaft teeth around the drive shaft from an opposing set of housing teeth around an aperture of the housing from which the drive shaft extends and initiates the active state of the IO access device. The IO needle is configured to rotate in the active state of the IO access device and provide IO access to a medullary cavity of a patient by way of drilling with the IO needle.

In some embodiments, a combination of a molded piece within the housing and an extension pin disposed in the axial channel of the output spool between the drive shaft and the molded piece is configured to stop over insertion of the drive shaft into the axial channel of the output spool. In addition, the combination of the extension pin and the molded piece is configured to decouple the force applied to the distal-end portion of the drive shaft from the constant-torque spring assembly.

In some embodiments, the compression spring is configured to relax when the force applied to the distal-end portion of the drive shaft is removed. This reengages the set of drive-shaft teeth with the set of housing teeth and reinitiates the inactive state of the IO access device.

In some embodiments, the IO access device is configured such that entry of the IO needle into the medullary cavity of the patient automatically removes the force applied to the distal-portion of the drive shaft.

Also disclosed herein is a method of an IO access device including, in some embodiments, an obtaining step of obtaining the IO access device. The IO access device includes a constant-torque spring assembly disposed in a housing, a drive shaft coupled to the constant-torque spring assembly and extending from the housing, and an IO needle coupled to the drive shaft. The method also includes an inserting step of inserting a distal end of the IO needle through skin at an insertion site of a patient. The method also includes an applying step of applying force to bone at the insertion site with the distal end of the IO needle. The applying step starts winding a metal ribbon of the constant-torque spring assembly from an output spool onto a storage spool, thereby starting rotation of the IO needle. The method also includes a drilling step of drilling through the bone until the IO needle enters a medullary cavity of the patient, thereby achieving IO access to the medullary cavity of the patient with the IO access device.

In some embodiments, the applying step inserts the drive shaft deeper into an axial channel of the output spool of the constant-torque spring assembly. The applying step also compresses a compression spring between a back side of a set of drive-shaft teeth around the drive shaft and the output spool. The applying step also disengages the set of drive-shaft teeth from an opposing set of housing teeth around an aperture of the housing from which the drive shaft extends to start the rotation of the IO needle.

In some embodiments, the method further includes a ceasing step of ceasing to apply the force to the bone with the distal end of the IO needle. The ceasing step removes at least a portion of the drive shaft from the axial channel of the output spool, relaxes the compression spring, and reengages the set of drive-shaft teeth with the set of housing teeth to stop the rotation of the IO needle.

In some embodiments, the ceasing step is manually initiated by a clinician after feeling a change in tissue density upon entering the medullary cavity of the patient.

In some embodiments, the ceasing step is automatically initiated by the IO access device after experiencing a change in tissue density upon entering the medullary cavity of the patient.

In some embodiments, the method further includes a triggering step of triggering a trigger of an interlock of the IO access device. The triggering step releases a lock pin disposed between the trigger and the output spool allowing the force applied to the bone at the distal end of the IO needle to start the rotation of the IO needle.

In some embodiments, the method further includes a detaching step of detaching the IO needle from a remainder of the IO access device; a removing step of removing from the IO needle an obturator removably disposed in a cannula; a confirming step of confirming the cannula is disposed in the medullary cavity by aspirating bone marrow through a syringe; a securing step of securing the cannula to the patient; and a starting step of starting interosseous infusion as boluses with a same or different syringe.

These and other features of the concepts provided herein will become more apparent to those of skill in the art in view of the accompanying drawings and following description, which describe particular embodiments of such concepts in greater detail.

DRAWINGS

DESCRIPTION

Figure 1:
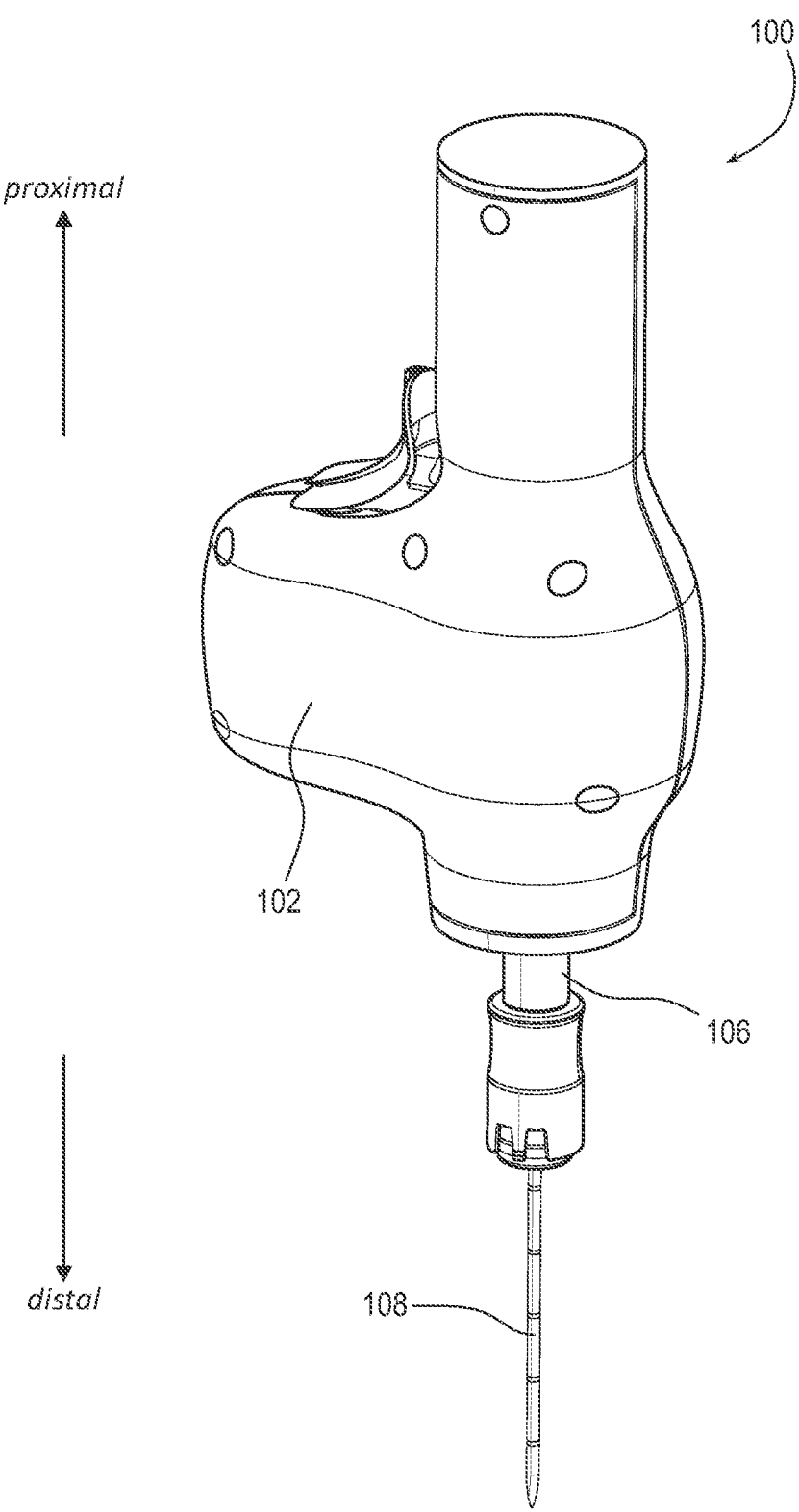
FIG. 1 illustrates a first IO access device in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, PIVC insertions are increasingly challenging in emergency scenarios as critically ill patients deteriorate. Intraosseous ("IO") access is often the only means available to clinicians to increase the patient's chances of recovery and even save the patients' lives. However, better tuned medical devices are needed that can significantly reduce design and manufacturing complexity while optimizing user experience. Disclosed herein are constant-torque IO access devices and methods thereof that address the forgoing shortcomings.

IO Access Devices

Figure 2:
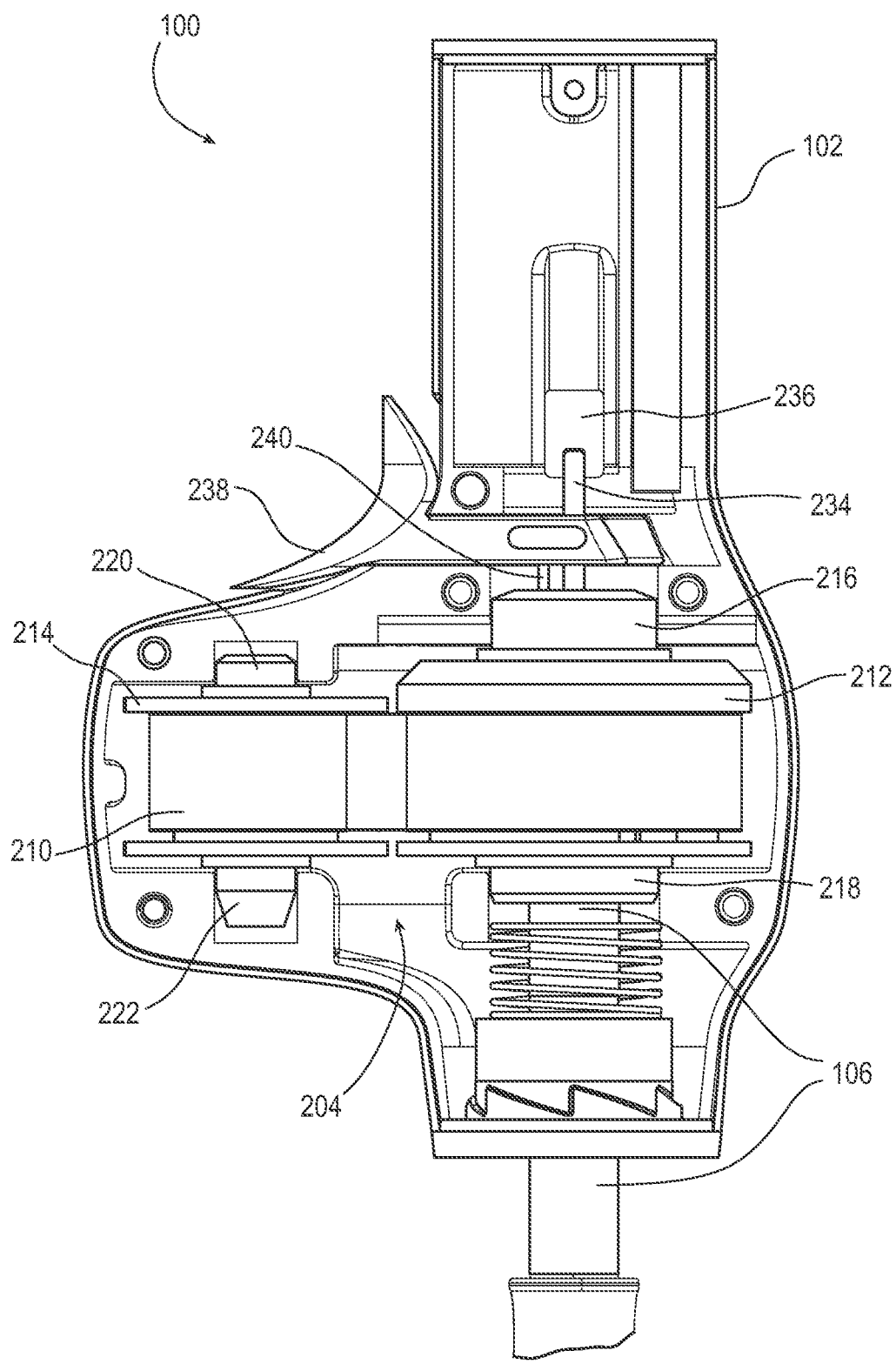
FIG. 2 illustrates the first IO access device with a side of housing removed in accordance with some embodiments.
Figure 3:
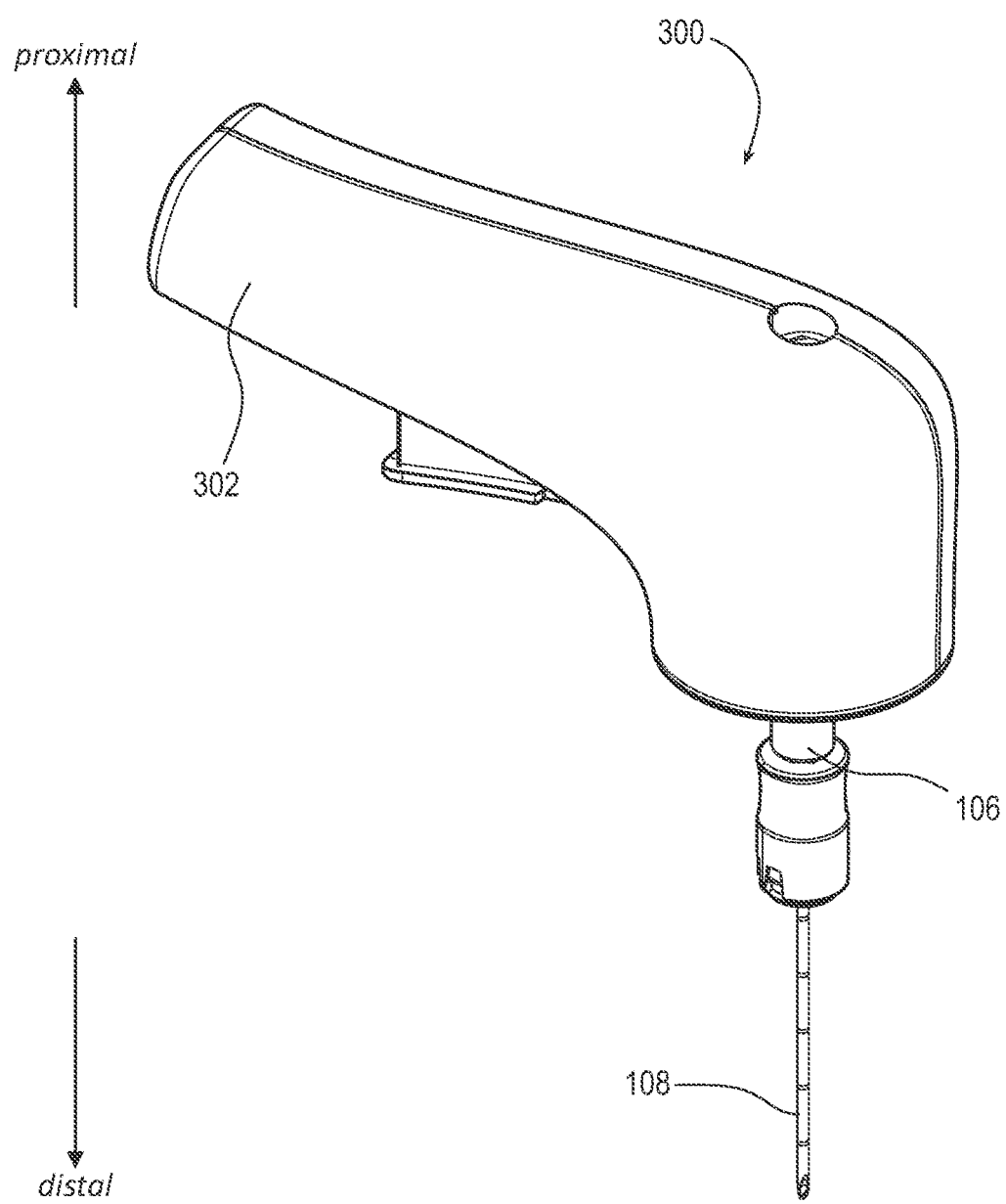
FIG. 3 illustrates a second IO access device in accordance with some embodiments.
Figure 4:
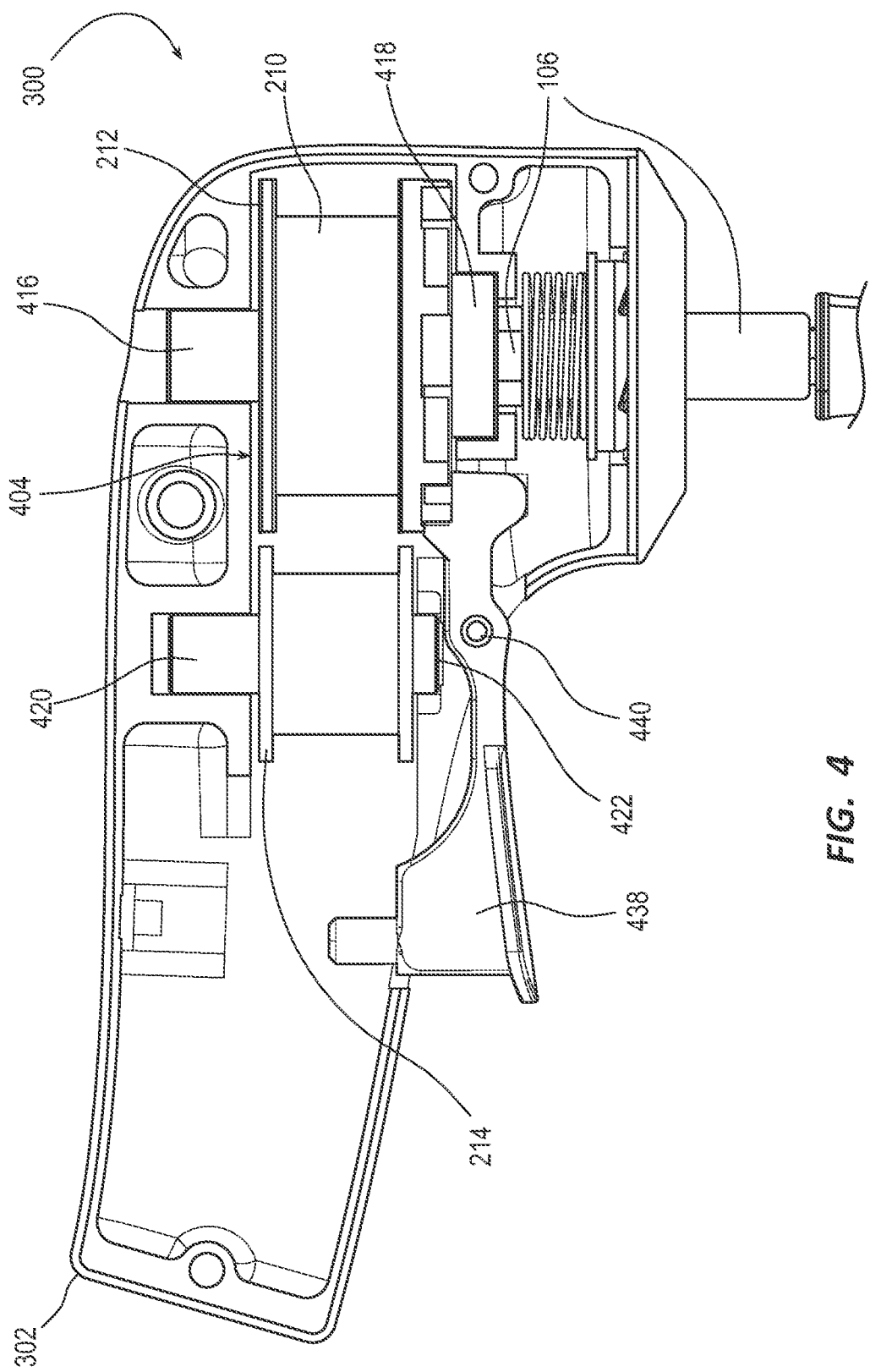
FIG. 4 illustrates the first IO access device with a side of housing removed in accordance with some embodiments.
Figure 5:
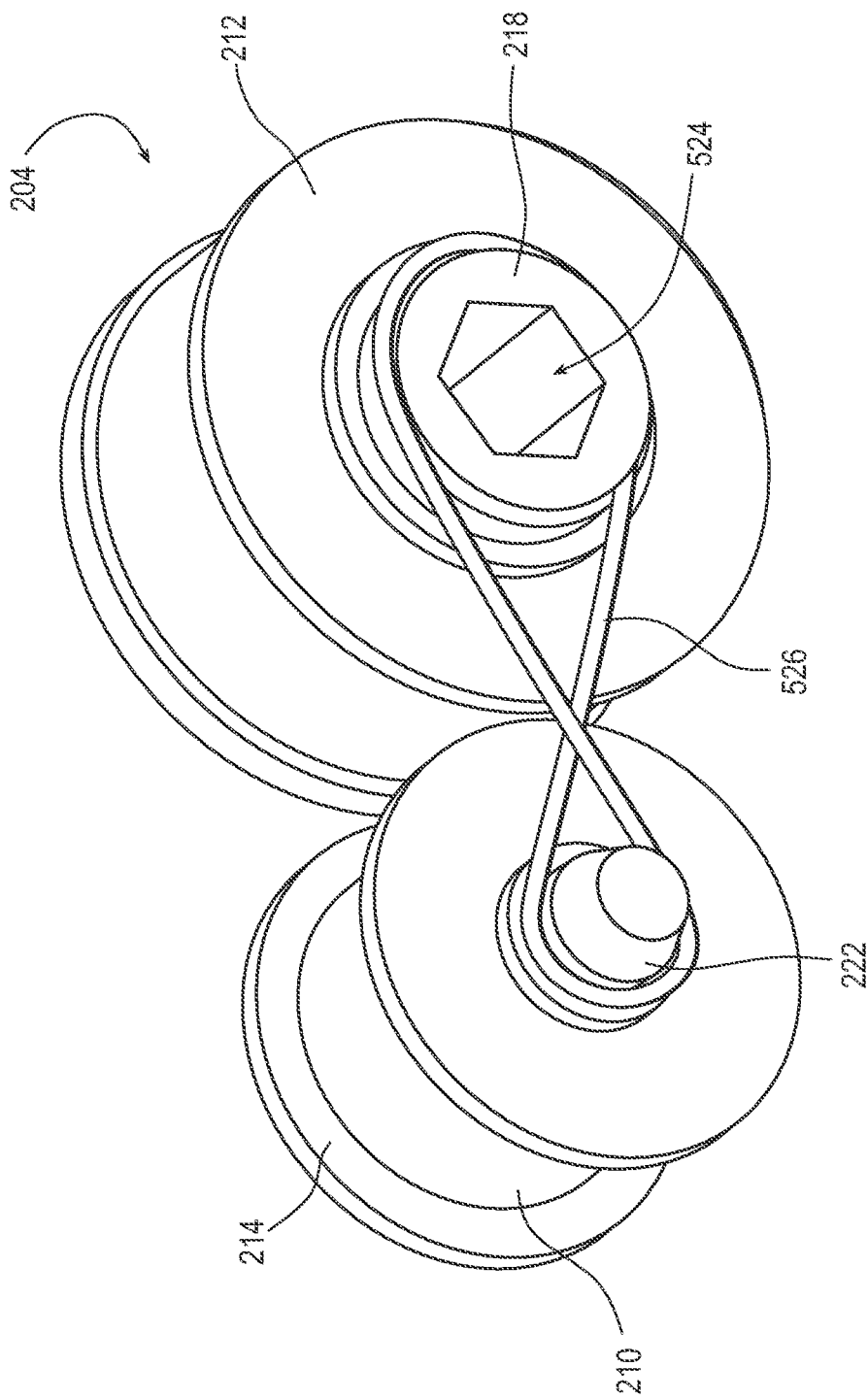
FIG. 5 illustrates a constant-torque spring assembly in accordance with some embodiments.

FIG. 1 and FIG. 3 respectively illustrate a first IO access device 100 and a second IO access device 300 in accordance with some embodiments. FIG. 2 and FIG. 4 respectively illustrate the first IO access device 100 and the second IO access device 300 with a side of housing 102 or 302 removed in accordance with some embodiments. FIG. 5 illustrates a constant-torque spring assembly 204 in accordance with some embodiments.

As shown, the IO access device 100 or 300 includes the constant-torque spring assembly 204 or 404 disposed in the housing 102 or 302, a drive shaft 106 extending from the housing 102 or 302, and an IO needle 108 coupled to the drive shaft 106 configured to provide IO access to a medullary cavity of a patient.

The housing 102 or 302 houses components of the IO access device 100 or 300. While the components of the IO access devices 100 and 300 are largely the same in terms of function, the components can be physically different in order to accommodate a particular form factor. For example, the IO access device 100 has a form factor for holding the IO access device 100 in a way that permits the IO needle 108 to access a medullary cavity of a patient with a stabbing motion. In contrast, the IO access device 300 has a form factor for holding the IO access device 100 in a way that permits the IO needle 108 to access a medullary cavity of a patient with in a more traditional drilling motion. The housing 102 or 302 is molded of a medically acceptable polymer such that sagittal halves of the housing 102 or 302 can be snapped or bound (e.g., mechanically fastened with fasteners, chemically bonded by adhesive, etc.) together around the components of the IO access device 100 or 300.

The constant-torque spring assembly 204 or 404 includes a metal ribbon (e.g., a stainless-steel ribbon) 210, at least a portion of which is reversely wound onto an output spool 212 and correctly wound onto a storage spool 214 with respect to a bias of the metal ribbon 210. The metal ribbon 210 is configured to wind onto the storage spool 214 or into a storage cavity with a constant torque across a range of revolutions-per-minute ("RPMs") when the output spool 212 is released or otherwise allowed to do so.

The constant-torque spring assembly 204 or 404 is unique in that stresses associated with deflection of the metal ribbon 210 are not cumulative over an entire length of the metal ribbon 210. The stresses are temporary and apply to only a short length (e.g., the exposed length) of the metal ribbon 210 at any given time. In addition, the metal ribbon 210 can be tuned with respect to any characteristic selected from its thickness, width, number of winds around the output spool 212, and the like for configuration of the constant-torque spring assembly 204 or 404 with an optimal rotary action of the IO needle for IO insertion.

Each spool of the output spool 212 and the storage spool 214 optionally includes a spindle co-incident with an axis of the spool for mounting the spool in the housing 102 or 302. Such a spindle can be on one side of the spool or both sides of the spool. For example, the constant-torque spring assembly 204 of the IO access device 100 includes spindle 216 and spindle 218 of the output spool 212 and spindle 220 and spindle 222 of the storage spool 214. Likewise, the constant-torque spring assembly 404 of the IO access device 300 includes spindle 416 and spindle 418 of the output spool 212 and spindle 420 and spindle 422 of the storage spool 214.

Alternatively or additionally to the foregoing spindles, each spool of the output spool 212 and the storage spool 214 optionally includes an axial channel co-incident with the axis of the spool, which can be for mounting the spool in the housing 102 or 302, driving another component (e.g., the drive shaft 106) of the IO access device 100 or 300, etc. Such an axial channel can be in one side of the spool, both sides of the spool, or extending from one side of the spool to the other side of the spool. For example, the constant-torque spring assembly 204 or 404 of the IO access device 100 or 300 includes an axial channel 524, which, in at least this case, includes a hexagonal shape to drive the hexagonal proximal-end portion of the drive shaft 106. (See FIGS. 5 and 6.) If the output spool 212 or the storage spool 214 includes a spindle on a side of the spool 212 or 214 and an axial channel in the same side of the spool 212 or 214, the spindle has an outer diameter large enough to accommodate an inner diameter of the axial channel as shown in FIG. 5 by the spindle 218 and the axial channel 524.

As shown in FIG. 5, same-side spindles such as the spindles 218 and 222 respectively of the output spool 212 and the storage spool 214 can be coupled together by at least one elastomeric loop 526 (e.g., an 'O'-ring) to prevent any timing-related errors between the output spool 212 and the storage spool 214. Such timing-related errors are possible if the metal ribbon 210 winds onto the storage spool 214 more slowly than the metal ribbon 210 winds off the output spool 212—or vice versa. As shown, the elastomeric loop 526 includes a half twist such that it crosses over itself to match the rotational motion of both the output spool 212 and the storage spool 214.

Figure 6:
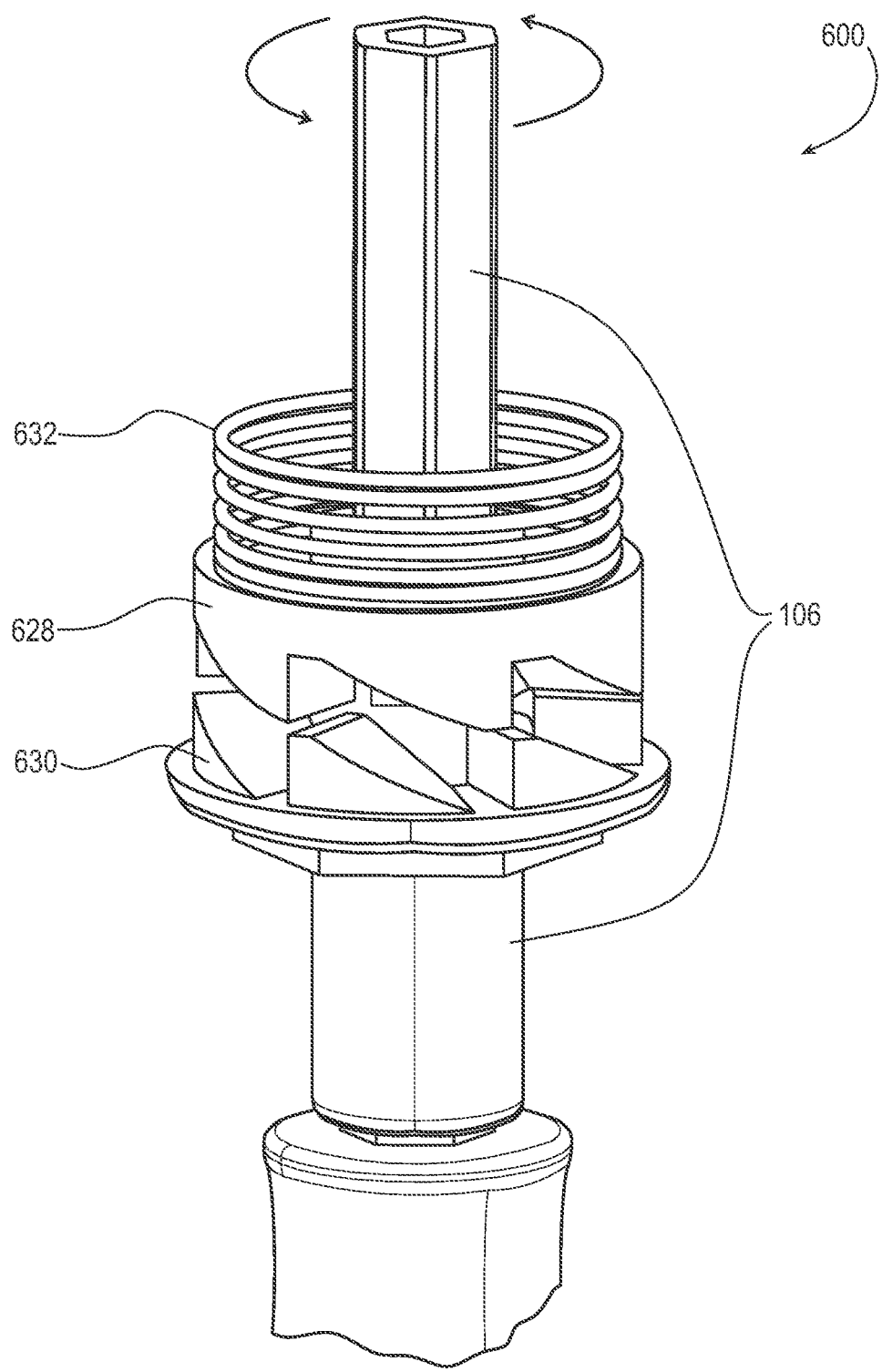
FIG. 6 illustrates an activation mechanism in accordance with some embodiments.

FIG. 6 illustrates an activation mechanism 600 for activating rotation of the IO needle 108 in accordance with some embodiments.

As shown, the activation mechanism 600 for activating rotation of the IO needle 108 includes the drive shaft 106 slideably disposed in the axial channel 524 of the output spool 212, a set of drive-shaft teeth 628 around the drive shaft 106, a set of opposing but complementary housing teeth 630 around an aperture of the housing 102 or 302 from which the drive shaft 106 extends, and a compression spring 632 between a back side of the set of drive-shaft teeth 628 and the output spool 212.

In an inactive state of the IO access device 100 or 300, a spring force is exerted on the back side of the set of drive-shaft teeth 628 by extension of the compression spring 632 between the back side of the set of drive-shaft teeth 628 and the output spool 212. Extension of the compression spring 632 keeps the drive shaft 106 pushed out of the axial channel 524, which also keeps the set of drive-shaft teeth 628 thereof away from the output spool 212 such that the set of drive-shaft teeth 628 and the set of housing teeth 630 are engaged with each other. Each set of teeth of the set of drive-shaft teeth 628 and the set of housing teeth 630 can include sawtooth-shaped teeth. When such sets of teeth are engaged with each other as in the inactive state of the IO access device 100 or 300, rotation of the drive shaft 106 and, thus, the rotation of the IO needle 108 is prevented.

In an active state of the IO access device 100 or 300, the spring force exerted on the back side of the set of drive-shaft teeth 628 by the extension of the compression spring 632 is overwhelmed by force applied to a distal-end portion of the drive shaft 106 by way of a distal end of the IO needle 108. Compression of the compression spring 632 keeps the drive shaft 106 pushed into the axial channel 524, which also keeps the set of drive-shaft teeth 628 thereof close to the output spool 212 such that the set of drive-shaft teeth 628 and the set of housing teeth 630 are disengaged with each other. When such sets of teeth are disengaged with each other as in the active state of the IO access device 100 or 300, rotation of the drive shaft 106 and, thus, the rotation of the IO needle 108 is allowed.

In a transition between the inactive state and the active state of the IO access device 100 or 300, force applied to the distal-end portion of the drive shaft 106 by way of, for example, engaging bone with the distal end of the IO needle 108, simultaneously inserts the drive shaft 106 deeper into the axial channel 524 and compresses the compression spring 632 between the back side of the set of drive-shaft teeth 628 and the output spool 212. Inserting the drive shaft 106 deeper into the axial channel disengages the set of drive-shaft teeth 628 from the set of housing teeth 630 to initiate the active state of the IO access device 100 or 300, in which state rotation of the IO needle 108 is effectuated by the output spool 212 of the constant-torque spring assembly 204 or 404 on the drive shaft 106.

In a transition between the active state and the inactive state of the IO access device 100 or 300, force removed from the distal-end portion of the drive shaft 106 by way of, for example, disengaging the distal end of the IO needle 108 from bone, allows the compression spring 632 between the back side of the set of drive-shaft teeth 628 and the output spool 212 to relax, which pushes the drive shaft 106 out of the axial channel 524 away from the output spool 212. Pushing the drive shaft 106 out of the axial channel 524 reengages the set of drive-shaft teeth 628 with the set of housing teeth 630 to initiate the inactive state of the IO access device 100 or 300, in which state rotation of the IO needle 108 is by the output spool 212 of the constant-torque spring assembly 204 or 404 on the drive shaft 106 is prevented.

The transition between the active state and the inactive state of the IO access device 100 or 300 can be automatically initiated by the IO access device 100 or 300. In such an IO access device, the compression spring 632 is configured by way of its material, construction, or both to have a spring constant and a compressible length proportional to a spring force greater than an average force that can be applied on the distal end of the IO needle 108 by marrow in a medullary cavity of a patient. Entry of the IO needle 108 into the medullary cavity of the patient automatically replaces the force applied on the distal end of the IO needle 108 by compact bone, which force is greater than the foregoing spring force, with the force applied on the distal end of the IO needle 108 by the marrow in the medullary cavity, which force is less than the foregoing spring force, thereby allowing the compression spring 632 to push the drive shaft 106 out of the axial channel 524 away from the output spool 212 to initiate the transition to the inactive state of the IO access device 100 or 300. Notwithstanding the foregoing, the transition between the active state and the inactive state can be manually initiated by a clinician after feeling a change in tissue density upon entering the medullary cavity from compact bone.

As shown in FIG. 2 for at least the IO access device 100, a combination of a molded piece 236 within the housing 102 and an extension pin 234 disposed in the axial channel 524 of the output spool 212 between the drive shaft 106 and the molded piece 236 is configured to stop over insertion of the drive shaft 106 into the axial channel 524 of the output spool 212 during the transition between the inactive state and the active state of the IO access device 100. In addition to stopping the over insertion of the drive shaft 106 into the axial channel 524 of the output spool 212, the combination of the extension pin 234 and the molded piece 236 is configured to decouple the force applied to the distal end of the IO needle 108 from the constant-torque spring assembly 204. That is, any further force applied to the distal end of the IO needle 108 than that needed for the transition between the inactive state and the active state of the IO access device 100 is applied to the molded piece 236 of the housing 102 by the extension pin 234 instead of the constant-torque spring assembly 204. Indeed, minimization of bearing surface area and reduction of extraneous moment arm lengths further decouple the force applied to the distal end of the 10 needle 108 from the constant-torque spring assembly 204.

As shown in FIG. 2, the IO access device 100 further includes an interlock including a trigger 238 and a lock pin 240 disposed between the trigger 238 and the output spool 212 in the inactive state of the IO access device 100. When pressed toward the housing, the trigger 238 is configured to release the lock pin 240 allowing the force applied to the distal end of the 10 needle 108 to simultaneously compress the compression spring 632 and insert the drive shaft 106 deeper into the axial channel 524.

As shown in FIG. 4, the IO access device 300 further includes an interlock including a trigger 438 pivotally mounted on a transversely oriented pin 440 disposed between the trigger 438 and the output spool 212. Both the trigger 438 and the output spool 212 have interlocking teeth that are interlocked in the inactive state of the IO access device 300. When pressed toward the housing, the trigger 438 is configured to pivot about the pin 440 and withdraw the interlocking teeth of the trigger 438 from those of the storage spool 214 allowing the force applied to the distal end of the 10 needle 108 to simultaneously compress the compression spring 632 and insert the drive shaft 106 deeper into the axial channel 524.

While not shown, the IO access device 100 or 300 can further include a hand-actuated braking system configured to act on the output spool 212 to slow the metal ribbon 210 from winding onto the storage spool 214. The braking system can be initiated at a start of the winding of the metal ribbon 210 onto the storage spool 214 or at any time throughout the winding.

The IO needle 108 is configured to separate from the IO access device 100 or 300 subsequent to achieving IO access to a medullary cavity of a patient. While not shown, the IO needle 108 includes an obturator removably disposed in a cannula. The cannula has a lumen configured for at least interosseous infusion upon removal of the obturator.

Methods

Methods of the IO access device 100 or 300 include at least a method of using the IO access device 100 or 300.

A method of using the IO access device 100 or 300 includes at least an obtaining step of obtaining the IO access device 100 or 300.

The method can also include a preparing step of preparing skin of the patient with an antiseptic (e.g., iodopovidone) at an insertion site of a patient. The insertion site can be about the proximal tibia, the distal tibia, or the distal femur.

The method can also include an inserting step of inserting the distal end of the IO needle 108 through the skin at the insertion site.

The method can also include an applying step of applying force to bone at the insertion site with the distal end of the IO needle 108. In accordance with applying the force to the bone at the insertion site, the applying step includes inserting the drive shaft 106 deeper into the axial channel 524 of the output spool 212 of the constant-torque spring assembly 204 or 404. The applying step also compresses the compression spring 632 between the back side of the set of drive-shaft teeth 628 around the drive shaft 106 and the output spool 212. The applying step also disengages the set of drive-shaft teeth 628 from the opposing set of housing teeth 630 around the aperture of the housing 102 or 302 from which the drive shaft 106 extends to start the rotation of the IO needle 108. The applying step starts winding the metal ribbon 210 of the constant-torque spring assembly 204 or 404 from the output spool 212 onto the storage spool 214, thereby starting rotation of the IO needle 108.

The method can also include a drilling step of drilling through the bone until the IO needle 108 enters a medullary cavity of the patient, thereby achieving IO access to the medullary cavity of the patient with the IO access device 100 or 300.

The method can also include a ceasing step of ceasing to apply the force to the bone with the distal end of the IO needle 108. The ceasing step removes at least a portion of the drive shaft 106 from the axial channel 524 of the output spool 212, relaxes the compression spring 632, and reengages the set of drive-shaft teeth 628 with the set of housing teeth 630 to stop the rotation of the IO needle 108. The ceasing step can be automatically initiated by the IO access device 100 or 300 after experiencing a change in tissue density (e.g., compact bone to marrow) upon entering the medullary cavity of the patient. The ceasing step can alternatively be manually initiated by a clinician after feeling the change in tissue density upon entering the medullary cavity of the patient.

The method can also include a triggering step of triggering the trigger 238 or 438 of the interlock of the IO access device 100 or 300. With respect to at least the IO access device 100, the triggering step releases the lock pin 240 disposed between the trigger 238 and the output spool 212 allowing the force applied to the bone at the distal end of the TO needle 108 to start the rotation of the IO needle 108.

The method can also include a detaching step of detaching the TO needle 108 from a remainder of the TO access device 100 or 300.

The method can also include a removing step of removing from the TO needle 108 the obturator removably disposed in the cannula.

The method can also include a confirming step of confirming the cannula is disposed in the medullary cavity by aspirating bone marrow through a syringe.

The method can also include a securing step of securing the cannula to the patient with a dressing.

The method can also include a starting step of starting interosseous infusion as boluses with a same or different syringe.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An intraosseous access device, comprising:
 a constant-torque spring assembly disposed in a housing, the constant-torque spring assembly comprising a metal ribbon reversely wound onto an output spool, the metal ribbon configured to wind onto a storage spool with a constant torque when the output spool is released, wherein spindles of the output spool and the storage spool are coupled together by at least one elastomeric loop to prevent any timing-related errors between the output spool and the storage spool;
 a drive shaft extending from the housing, the drive shaft coupled to the constant-torque spring assembly; and
 an intraosseous needle coupled to the drive shaft configured to provide intraosseous access to a medullary cavity of a patient.

2. The intraosseous access device of claim 1, wherein the housing includes a set of housing teeth around an aperture of the housing from which the drive shaft extends and the drive shaft includes a set of complementary drive-shaft teeth around the drive shaft opposing the set of housing teeth, the set of housing teeth and the set of drive-shaft teeth engaged in an inactive state of the intraosseous access device by a compression spring between a back side of the set of drive-shaft teeth and the output spool.

3. The intraosseous access device of claim 2, wherein the drive shaft is slideably disposed in an axial channel of the output spool such that force applied to a distal end of the intraosseous needle simultaneously compresses the compression spring and inserts the drive shaft deeper into the axial channel, thereby disengaging the set of drive-shaft teeth from the set of housing teeth and initiating an active state of the intraosseous access device in which rotation of the intraosseous needle is effectuated by the output spool of the constant-torque spring assembly on the drive shaft.

4. The intraosseous access device of claim 3, wherein a combination of a molded piece within the housing and an extension pin disposed in the axial channel of the output spool between the drive shaft and the molded piece is configured to stop over insertion of the drive shaft into the axial channel of the output spool as well as decouple the force applied to the distal end of the intraosseous needle from the constant-torque spring assembly.

5. The intraosseous access device of claim 3, wherein the compression spring is configured to relax when the force applied to the distal end of the intraosseous needle is removed, thereby reengaging the set of drive-shaft teeth with the set of housing teeth and reinitiating the inactive state of the intraosseous access device.

6. The intraosseous access device of claim 3, wherein the intraosseous access device is configured such that entry of the intraosseous needle into the medullary cavity of the patient automatically removes the force applied to the distal end of the intraosseous needle.

7. The intraosseous access device of claim 3, further comprising an interlock including a trigger and a lock pin disposed between the trigger and the output spool in the inactive state of the intraosseous access device, the trigger configured to release the lock pin allowing the force applied to the distal end of the intraosseous needle to simultaneously compress the compression spring and insert the drive shaft deeper into the axial channel.

8. The intraosseous access device of claim 1, further comprising a braking system configured to act on the output spool to slow the metal ribbon from winding onto the storage spool.

9. The intraosseous access device of claim 1, wherein the intraosseous needle is configured to separate from the intraosseous access device subsequent to achieving intraosseous access to the medullary cavity of the patient.

10. The intraosseous access device of claim 1, wherein the intraosseous needle includes an obturator removably disposed in a cannula having a lumen configured for at least interosseous infusion upon removal of the obturator.

11. An intraosseous access device, comprising:
a constant-torque spring assembly disposed in a housing, the constant-torque spring assembly including a metal ribbon reversely wound onto an output spool configured to wind onto a storage spool with a constant torque in an active state of the intraosseous access device;
a drive shaft extending from the housing, the drive shaft slideably disposed in an axial channel of the output spool such that force applied to a distal-end portion of the drive shaft simultaneously compresses a compression spring and inserts the drive shaft deeper into the axial channel, thereby disengaging a set of drive-shaft teeth around the drive shaft from an opposing set of housing teeth around an aperture of the housing from which the drive shaft extends and initiating the active state of the intraosseous access device; and
an intraosseous needle coupled to the distal-end portion of the drive shaft configured to rotate in the active state of the intraosseous access device and provide intraosseous access to a medullary cavity of a patient by way of drilling with the intraosseous needle.

12. The intraosseous access device of claim 11, wherein a combination of a molded piece within the housing and an extension pin disposed in the axial channel of the output spool between the drive shaft and the molded piece is configured to stop over insertion of the drive shaft into the axial channel of the output spool as well as decouple the force applied to the distal-end portion of the drive shaft from the constant-torque spring assembly.

13. The intraosseous access device of claim 11, wherein the compression spring is configured to relax when the force applied to the distal-end portion of the drive shaft is removed, thereby reengaging the set of drive-shaft teeth with the set of housing teeth and initiating an inactive state of the intraosseous access device.

14. The intraosseous access device of claim 11, wherein the intraosseous access device is configured such that entry of the intraosseous needle into the medullary cavity of the patient automatically removes the force applied to the distal-end portion of the drive shaft.

15. An intraosseous access device, comprising:
a constant-torque spring assembly disposed in a housing, the constant-torque spring assembly comprising a metal ribbon reversely wound onto an output spool, the metal ribbon configured to wind onto a storage spool with a constant torque when the output spool is released;
a drive shaft extending from the housing, the drive shaft coupled to the constant-torque spring assembly, wherein the housing includes a set of housing teeth around an aperture of the housing from which the drive shaft extends and the drive shaft includes a set of complementary drive-shaft teeth around the drive shaft opposing the set of housing teeth, the set of housing teeth and the set of drive-shaft teeth engaged in an inactive state of the intraosseous access device by a compression spring between a back side of the set of drive-shaft teeth and the output spool; and
an intraosseous needle coupled to the drive shaft configured to provide intraosseous access to a medullary cavity of a patient, wherein the drive shaft is slideably disposed in an axial channel of the output spool such that force applied to a distal end of the intraosseous needle simultaneously compresses the compression spring and inserts the drive shaft deeper into the axial channel, thereby disengaging the set of drive-shaft teeth from the set of housing teeth and initiating an active state of the intraosseous access device in which rotation of the intraosseous needle is effectuated by the output spool of the constant-torque spring assembly on the drive shaft.

16. The intraosseous access device of claim 15, wherein a combination of a molded piece within the housing and an extension pin disposed in the axial channel of the output spool between the drive shaft and the molded piece is configured to stop over insertion of the drive shaft into the axial channel of the output spool as well as decouple the force applied to the distal end of the intraosseous needle from the constant-torque spring assembly.

17. The intraosseous access device of claim 15, wherein the compression spring is configured to relax when the force applied to the distal end of the intraosseous needle is removed, thereby reengaging the set of drive-shaft teeth with the set of housing teeth and reinitiating the inactive state of the intraosseous access device.

18. The intraosseous access device of claim 15, wherein the intraosseous access device is configured such that entry of the intraosseous needle into the medullary cavity of the patient automatically removes the force applied to the distal end of the intraosseous needle.

19. The intraosseous access device of claim 15, further comprising an interlock including a trigger and a lock pin disposed between the trigger and the output spool in the inactive state of the intraosseous access device, the trigger configured to release the lock pin allowing the force applied to the distal end of the intraosseous needle to simultaneously compress the compression spring and insert the drive shaft deeper into the axial channel.

\* \* \* \* \*